United States Patent [19]

Blau et al.

[11] Patent Number: 4,679,568

[45] Date of Patent: Jul. 14, 1987

[54] PHYSIOLOGICAL POTENTIAL PREAMPLIFIER

[75] Inventors: David A. Blau, Los Altos; William R. Fish, San Jose, both of Calif.

[73] Assignee: Siegen Corporation, Sunnyvale, Calif.

[21] Appl. No.: 777,773

[22] Filed: Sep. 19, 1985

[51] Int. Cl.$^4$ ............................................. A61B 5/04
[52] U.S. Cl. .................................. 128/696; 128/908; 128/419 D
[58] Field of Search .................. 128/303.13–303.19, 128/419 D, 696, 901, 902, 908

[56] References Cited

U.S. PATENT DOCUMENTS

| | | | |
|---|---|---|---|
| 3,236,239 | 2/1966 | Berkovits | 128/419 D |
| 3,521,087 | 7/1970 | Lombardi | 128/908 |
| 3,699,389 | 10/1972 | Holsinger | 128/908 |
| 3,703,900 | 11/1972 | Holznagel | 128/419 D |
| 3,744,482 | 7/1973 | Kaufman et al. | 128/639 |
| 3,808,502 | 4/1974 | Babilius | 128/908 |
| 3,872,251 | 3/1975 | Auerbach et al. | 128/904 |
| 4,200,109 | 4/1980 | McMorrow, Jr. | 128/908 |
| 4,367,752 | 1/1983 | Jimenez et al. | 128/706 |
| 4,372,324 | 2/1983 | Rockwell | 128/419 D |
| 4,440,172 | 4/1984 | Langer | 128/908 |

Primary Examiner—Edward M. Coven
Attorney, Agent, or Firm—Thomas E. Schatzel

[57] ABSTRACT

Disclosed is a preamplifier which is responsive to a physiological potential developed by a subject and operative to develop a potential suitably isolated therefrom, the preamplifier including a pair of input networks for receiving therebetween the physiological potential, a pair of operational amplifiers each connected in a unity (voltage) gain, voltage follower, configuration and each driven by a respective one of the input networks, a low resistance resistor connected between the voltage followers to directly develop from the potential a current of suitable level for directly driving an optical isolator, and an optical isolator having an input portion which is connected in the feedback path of one of the operational amplifiers so as to be driven by the current and an output portion at which the optical isolator develops the isolated potential.

7 Claims, 3 Drawing Figures

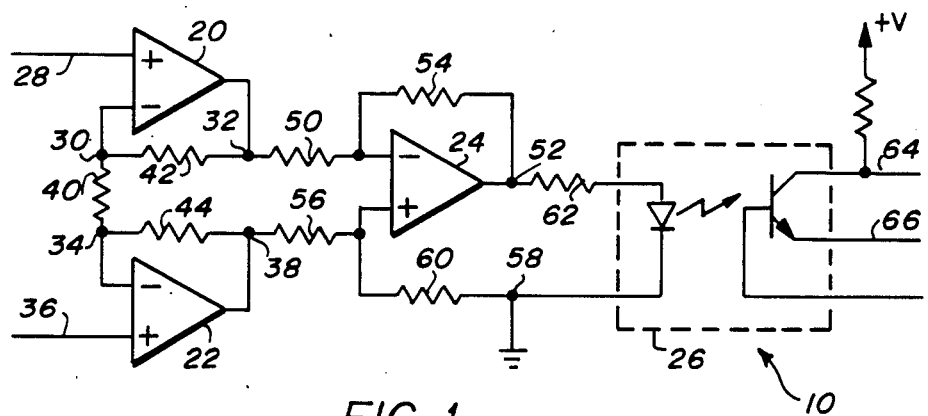
FIG_1 (PRIOR ART)
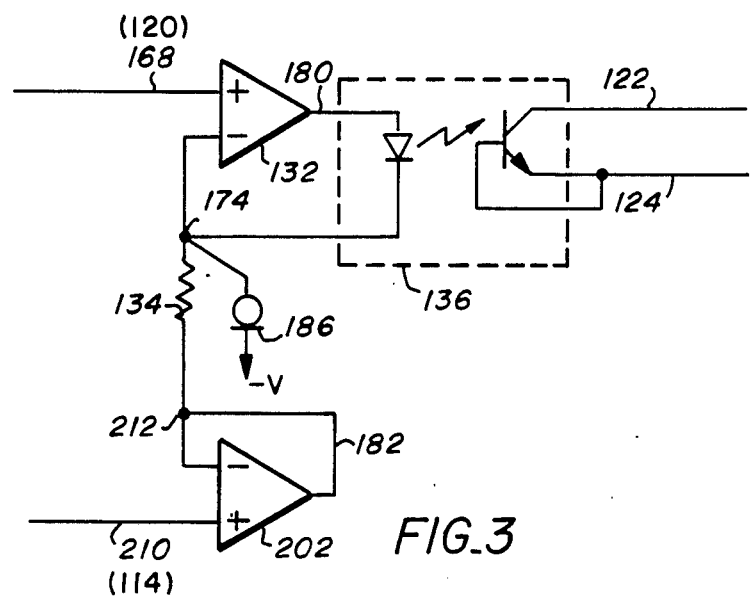
FIG_3

PHYSIOLOGICAL POTENTIAL PREAMPLIFIER

BACKGROUND OF THE INVENTION

1. Field of the Invention

The present invention relates to medical instruments generally and more particularly to a preamplifier of reduced size for use therewith.

2. Description of the Prior Art

Evoked-potential-type medical instruments are of increasing importance as diagnostic tools. Such instruments test a portion of a subject's neurological system. More particularly, such instruments stimulate, at a periodic rate, one of the subject's senses (hearing, sight, touch, etc.). Further, such instruments receive physiological (electroencephalograph (EGG), electromyography, and/or electrocardiography (EKG)) potentials generated by the subject. Finally, such instruments synchronously detect the received potentials to separate therefrom those potentials which are generated by the subject in response to the stimulus, in other words, the evoked potentials. Based upon the characteristics of the evoked potentials, including their amplitude, shape, and delay, deductions may be made as to the integrity of the specific neurological system and as to the presence of certain diseases which affect it.

For coupling physiological potentials generated by the subject to the instrument while electrically isolating the subject from the instrument, medical instruments commonly employ a number of (instrumentation-type) preamplifiers. Typical thereof is the prior-art-type preamplifier which is illustrated in FIG. 1 and which is designated generally by the number 10. Preamplifier 10 is shown to include as principal components three operational-type amplifiers, which are respectively designated 20, 22, and 24 and an optical isolator, which is designated 26. Operational amplifier 20 is configured with the non-inverting input of the amplifier connected to a line 28, the inverting input of the amplifier connected to a node 30, and the output of the amplifier connected to a node 32. Operational amplifier 22 is configured with the inverting input of the amplifier connected to a node 34, the non-inverting input of the amplifier connected to a line 36, and the output of the amplifier connected to a node 38. Node 30 is both coupled to node 34 by a resistor 40 and coupled to node 32 by another resistor 42. Node 34 is also coupled to node 38 by still another resistor 44.

Operational amplifier 24 is configured with the amplifier inverting input both coupled to node 32 by a resistor 50 and coupled to a node 52 by a resistor 54, with the amplifier non-inverting input both coupled to node 38 by a resistor 56 and coupled to a node 58 by a resistor 60, and with the amplifier output connected to node 52. Node 52 is coupled to node 58 by the series combination of a resistor 62 and the input portion of optical isolator 26, the output portion of which is connected between a pair of lines 64 and 66. Node 58 is connected to circuit ground.

Resistor 40 has, typically, a resistance of 10K ohms. Typically, resistors 42 and 44 each have a resistance of 1 meg ohm; resistors 50 and 56 each have a resistance of 10K ohms, and, resistors 54 and 60 each have a resistance of 100K ohms.

When lines 28 and 36 are connected each to a respective one of a pair of electrodes that are suitably applied to the subject, an electrocephalograph potential, which is generated (differentially) between the electrodes by the subject, is received by preamplifier 10. Preamplifier 10, first, amplifies the (voltage) level of the received potential. With the abovementioned resistor resistances, operational amplifiers 20 and 22 develop between nodes 32 and 38 an amplified potential the (voltage) level of which is approximately 200 times that of the received potential developed between lines 28 and 36. (More specifically, at least to the extent that the amplifier approaches the ideal, operational amplifier 20 maintains the potential at node 32 at whatever potential is required to maintain the potential at node 30 at the same level as the potential which is developed on line 28. Also, operational amplifier 22 maintains node 34 at the line 36 potential. Thus, a potential is developed across resistor 40 which is similar to the potential that is developed between lines 28 and 36. Since, ideally, the currents flowing into or out of the non-inverting inputs of amplifiers 20 and 22 are negligible, the current which flows through resistor 40 must flow through resistors 42 and 44. This current develops a potential across resistor 42 which is equal to the resistor 40 potential times the ratio of the resistance of resistor 42 to that of resistor 40. A similar potential is developed across resistor 44.)

Operational amplifier 24 of preamplifier 10 further amplifies the (voltage) level of the received potential. With the above-mentioned resistor resistances, operational amplifier 24 develops between node 52 and node 58 (circuit ground) a further amplified potential the (voltage) level of which is approximately 10 times that of the amplified potential developed between nodes 32 and 38.

Finally, resistor 62 developes from the further amplified potential a current of suitable level for driving the input portion of optical isolator 26. From the current, optical isolator 26 develops between lines 64 and 66 a potential suitable for driving other portions of the instrument while suitably isolating therefrom the subject.

The above-mentioned prior-art-type preamplifier is disadvantageous for a number of reasons. For one, the relatively large voltage gain provided by operational amplifiers 20 and 22, and, even, operational amplifier 24, is at the expense of band width. As a consequence, preamplifier 10 has relatively poor (narrow) band width characteristics.

Also, preamplifier 10 has relatively poor common mode rejection characteristics. The relatively poor common mode rejection characteristics are due, at least in part, to the use of a reference potential, circuit ground potential (or any potential not related to the lines 28 and 36 potential). Also, common mode rejection characteristics suffer unless precision, matched and/or adjustable resistors are employed.

Additionally, preamplifier 10 is relatively noisy.

Further, preamplifier 10 is relatively complex and, as a consequence, relatively large. When combined with many other such preamplifiers that are required of some instruments, a package results which may be difficult to locate relatively near the subject. This is particularly the case where space is at a premium, such as in an operating room. Yet, the particularly electrically noisy environment of an operating room makes locating the preamplifier relatively near the subject even more important.

Finally, preamplifier 10 lacks the means for protecting the preamplifier from destructive potentials of the type which are generated when electrical-discharge-type (Bovie) knives or defibrillators are used.

SUMMARY OF THE PRESENT INVENTION

It is therefore a material object of the present invention to provide a preamplifier which is relatively simple and, thus, small.

Another object of the present invention is to provide a preamplifier which meets Food and Drug Administration (FDA) and Underwriters Laboratory (UL) requirements.

Another object of the present invention is to provide a preamplifier which has relatively good (wide) band width characteristics.

Another object of the present invention is to provide a preamplifier which has relatively good common mode rejection characteristics.

Another object of the present invention is to provide a preamplifier which is relatively quiet.

Still another object of the present invention is to provide a preamplifier which can survive the use of an electrical-discharge-type knife and a defibrillator.

Briefly, the presently preferred embodiment of the present invention includes a pair of input networks for receiving therebetween an evoked potential, a pair of operational amplifiers each connected in a unity (voltage) gain, voltage follower, configuration and each driven by a respective one of the input networks, a low resistance resistor connected between the voltage followers to directly develop from the potential a current of suitable level for directly driving an optical isolator, and an optical isolator having an input portion which is connected in the feedback path of one of the operational amplifiers so as to be driven by the current to develop an isolated potential at the output portion thereof.

A material advantage of the present invention is the ability it affords to provide a preamplifier which is relatively simple and, thus, small.

Other advantages of the present invention include the ability to provide a preamplifier which has relatively good band width, common mode rejection, and noise characteristics.

Still another advantage of the present invention is the ability it affords to provide a preamplifier which can survive the use of electrical-discharge-type knives and defibrillators.

These and other objects and advantages of the present invention will no doubt become apparent to those skilled in the art after having read the detailed description of the presently preferred embodiment which is illustrated in the figures of the drawing.

IN THE DRAWING

FIG. 1 is a schematic diagram illustrating a prior-art-type preamplifier;

FIG. 3 is a schematic diagram illustrating a basic embodiment of a preamplifier in accordance with the present invention.

DETAILED DESCRIPTION OF THE PREFERRED EMBODIMENT

Figure 2:
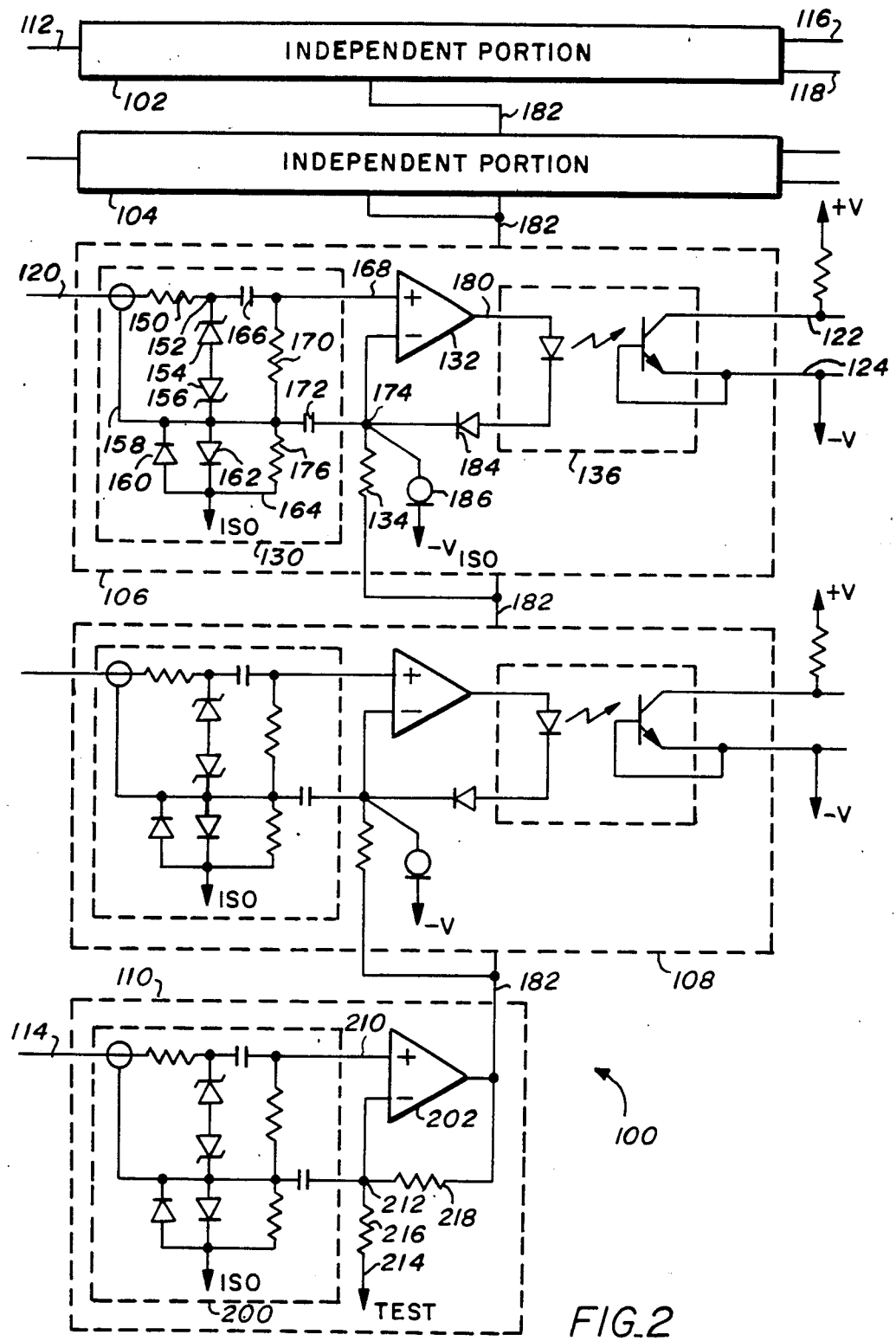
FIG. 2 is a schematic diagram illustrating the presently preferred embodiment of a four-channel preamplifier in accordance with the present invention.

Illustrated in FIG. 2 of the drawing generally designated by the number 100 is a four-channel preamplifier in accordance with the present invention. In the presently preferred embodiment, preamplifier 100 employs four, similar, "independent" portions, which are respectively designated 102, 104, 106, and 108, and a "shared" or "common" portion, which is designated 110. Each of the "independent" portions receives the potential developed between an associated input line and a "reference" or "common" line, and, responsive thereto, develops a suitably isolated potential between a pair of associated output lines. More particularly, portion 102 receives the potential developed between a line 112 and a line 114 and develops a potential between a pair of lines 116 and 118. Similarly, portion 106 receives the potential developed between a line 120 and line 114 and develops a potential between a pair of lines 122 and 124.

Typical of the "independent" portions, portion 106 is shown to include as principal components an input network 130, an operational amplifier 132, a resistor 134, and an optical isolator 136. Network 130 has an overload-current-limiting resistor 150 connected between line 120 and a node 152; a pair of overload-current-shunting, zener, diodes 154 and 156 connected in opposite directions, in series, between node 152 and a line 158; and a pair of overload-current-shunting, switching, diodes 160 and 162 connected back-to-back in parallel, between line 158 and a line 164. Further, network 130 has an AC-coupling capacitor 166 connected between node 152 and a line 168, a DC-biasing resistor 170 connected between lines 168 and 158, another AC-coupling capacitor 172 connected between line 158 and a node 174, and another DC-biasing resistor 176 connected between lines 158 and 164.

In the presently preferred embodiment, resistor 150 has a resistance of 1K ohm; each of diodes 152 and 154 is of the type which is commonly designated 1N746A; each of diodes 160 and 162 is of the type which is commonly designated 1N914; each of capacitors 166 and 172 has a capacitance of 0.1 mfd; and, each of resistors 170 and 176 has a resistance of 2 meg ohms.

Operational amplifier 132 is configured with the amplifier non-inverting input connected to network 130 by line 168, the amplifier inverting input connected to node 174, and the amplifier output connected to a line 180. Resistor 134 is connected between node 174 and a line 182. The input portion of optical isolator 136 is connected in series with a diode 184 between line 180 and node 174. The output portion of optical isolator 136 is connected in a diode configuration in which the emitter and the base of the phototransistor of the optical isolator are interconnected) between lines 122 and 124. Connected between node 174 and a negative power supply potential is a (constant) current (regulator) diode 186.

"Common" portion 110 is shown to include as principal components an input network 200, which is similar to network 130, and an operational amplifier 202. Operational amplifier 202 is configured with the amplifier non-inverting input connected to network 200 by a line 210, the amplifier inverting input connected to a node 212, and the amplifier output connected to line 182. Node 212 is both coupled to a line 214 by a resistor 216 and coupled to line 182 by another resistor 218.

In the presently preferred embodiment, operational amplifiers 132 and 202 are each of the type which is designated OPA2111B by the Burr Brown Company; resistor 134 is of the metal film type having a resistance of 2 ohms; and, optical isolator 136 is of the gallium-aluminum-arsenide type which is designated MCT5201 by the General Instruments Company. Preferably, diode 184 is of the type which is commonly designated 1N914; and, current diode 186 is of the 1.5 ma type which is commonly designated CR150. The resistance of resistor 216 is 1 meg ohm; and that of resistor 218 is 100 ohms.

Although not shown, an isolated power supply of the type which is commonly designated 722MG is also employed.

The operation of preamplifier 100 is best understood by first ignoring networks 130 and 200 except to assume that network 130 couples line 168 to line 120 and that network 200 couples line 210 to line 114. Also, ignore diodes 184 and 186. Further, ignore resistor 216 and assume the resistance of resistor 218 is negligible, or, that line 182 and, thus, the output of operational amplifier 202 is directly connected to node 212, as shown in FIG. 3 of the drawing.

Operational amplifier 132 maintains the potential on line 180 at whatever potential is required to maintain the potential at node 174 at the same level as the potential which is developed on line 168. Also, normally, operational amplifier 202 maintains line 182 at the line 210 potential. Thus, a potential is developed across resistor 134 which is similar to the potential that is developed between lines 120 and 114. As a consequence, an (AC) current is developed which flows out of operational amplifier 180, through the input portion of optical isolator 136, through diode 184, and through resistor 134. Due to the relatively low resistance of resistor 134, the level of the (AC) current is suitable for directly driving the input portion of the optical isolator.

Current diode 186 establishes a DC current flow for DC-biasing the input portion of optical isolator 136 to operate the isolator in a relatively linear portion of its operating range. Also, for more linear operation, the output portion of optical isolator 136 is connected in a diode configuration.

Diode 184 (shown in FIG. 2) prevents damaging reverse current from flowing through the input portion of optical isolator 136 such as might otherwise occur if preamplifier 100 were overloaded. In another embodiment, diode 184 is connected back-to-back, in parallel, with the input portion of optical isolator 136. Although providing faster recovery following an overload, the faster recovery is at the expense of additional power-supply current loading during overload.

Resistors 216 and 218 permit the injection of a testing or calibrating signal developed on line 214. The use of such a signal permits gain measurements to enable compensation for the initial tolerance or later ageing changes of optical isolator 136 and other components.

Resistor 150 limits the current which flows when preamplifier 100 is overloaded (such as when electrical-discharge-type knives or defibrillators are used). A shunt path for the overload current is provided by diodes 154 and 156. Because of their relatively low impedance, the diodes are (AC) coupled to the "bootstrap" output (node 174) of operational amplifier 132. One of diodes 160 and 162 conducts the overload current to line 164 which is connected to the subject (isolated) ground (by a grounding pad or leg band).

Capacitors 166 and 172 and resistors 170 and 176 provide low frequency roll-off (AC-coupling). The second resistor in conjunction with the second capacitor, which is connected to the "bootstrap" output, provide two-pole roll-off.

The line 120 sheld is (AC) coupled to the "bootstrap" output to reduce the noise pickup of line 120 while minimizing the capacitive effects the shield would otherwise have on the subject generated potential.

It is important to note that no where is an (AC) potential developed which is significantly larger than the potential developed between lines 120 and 114. Of course, a DC voltage drop is developed across the input portion of optical isolator 136 and diode 184. However, the AC impedance of these components is relatively small. Thus, the AC potential drop developed thereacross is negligible. As a consequence, preamplifier 100 has relatively good (wide) bandwidth characteristics.

Further, preamplifier 100 does not require precision, matched or adjustable components. The only compensation that need be made is for the initial tolerance of and ageing changes of optical isolator 136. The initial tolerance of optical isolator 136 and resistor 134 and the ageing changes of the optical isolator affect the gain of preamplifier 100, but not its common mode rejection characteristics.

After having read the preceding disclosure, certain alterations and modifications of the present invention will no doubt become apparent to those skilled in the art. It is therefore intended that the following claims be interpreted to include all such alterations and modifications as fall within the true spirit and scope of the invention.

We claim:

1. A preamplifier responsive to a potential developed between a first input line and a common line and operative to develop an isolated potential between a first pair of output lines, the preamplifier comprising in combination:
   first operational amplifier means including a non-inverting input, an inverting input, and an output;
   first coupling means coupling said first operational amplifier means non-inverting input to the common line;
   first resistor means including a first end coupled to said first operational amplifier means and a second end;
   second coupling means coupling said first operational amplifier means inverting input to said first operational amplifier means output;
   second operational amplifier means including a non-inverting input, an inverting input coupled to said first resistor means second end, and an output;
   third coupling means coupling said second operational amplifier means non-inverting input to the first input line;
   first optical isolator means including an input portion and an output connected between the first pair of output lines; and
   fourth coupling means coupling said first optical isolator means input portion between said second operational amplifier means inverting input and said operational amplifier means output.

2. A preamplifier as recited in claim 1 further comprising means for developing in said first optical isolator means input portion a DC biasing current of predetermined level.

3. A preamplifier as recited in claim 1 wherein the preamplifier is further responsive to a potential developed between a second input line and said common line and operative to develop an isolated potential between a second pair of output lines, the preamplifier further comprising:
   second resistor means including a first end coupled to said first operational amplifier means and a second end;

third operational amplifier means including a non-inverting input, an inverting input coupled to said second resistor means second end and an output;

fifth coupling means coupling said third operational amplifier non-inverting input to the second input line;

second optical isolator means including an input portion and an output portion connected between the second pair of output lines; and sixth coupling means coupling said second optical isolator means input portion between said third operational amplifier means inverting input and said third operational amplifier means output.

4. A preamplifier as recited in claim 1 wherein said second coupling means includes a second resistor connected between said first operational amplifier means inverting input and said first operational amplifier means output.

5. A preamplifier as recited in claim 1 wherein said fourth coupling means includes a diode connected in series with said first optical isolator means input portion between said second operational amplifier means inverting input and said second operational amplifier means output.

6. A preamplifier responsive to a potential developed between a first input line and a common line and operative to develop an isolated potential between a first pair of output lines, the preamplifier comprising in combination:

first operational amplifier means including a noninverting input connected to said common line, an inverting input, and an output coupled to said first operational amplifier means inverting input;

first resistor means including a first end coupled to said first operational amplifier means output and a second end, second operational amplifier means including a non-inverting input connected to said first input line, an inverting input coupled to said first resistor means second end, and an output; and first optical isolator means including an input portion coupled between said second operational amplifier means inverting input and said second operational amplifier means output and an output portion connected between the first pair of output lines.

7. A preamplifier as recited in claim 6 wherein the preamplifier is further responsive to a potential developed between a second input line and said common line and operative to develop an isolated potential between a second pair of output lines, the preamplifier further comprising second resistor means including a first end coupled to said first operational amplifier means output and a second end;

third operational amplifier means including a noninverting input connected to said second input line, an inverting input coupled to said second resistor second end, and an output; and second optical isolator means including an input portion coupled between said third operational amplifier means inverting input and said third operational amplifier means output and an output portion connected between the second pair of output lines.

* * * * *